United States Patent [19]

Kinami et al.

[11] Patent Number: 5,241,096

[45] Date of Patent: Aug. 31, 1993

[54] FLUORINE-CONTAINING ORGANOSILICON COMPOUND

[75] Inventors: Hitoshi Kinami, Annaka; Kouichi Yamaguchi, Takasaki; Hideki Fujii, Annaka; Shuji Suganuma, Takasaki; Yoshikazu Saito, Annaka, all of Japan

[73] Assignee: Shin-Etsu Chemical Co., Ltd., Tokyo, Japan

[21] Appl. No.: 961,369

[22] Filed: Oct. 15, 1992

[30] Foreign Application Priority Data

Oct. 17, 1991 [JP] Japan ................................. 3-298323

[51] Int. Cl.$^5$ ............................................. C07F 7/08
[52] U.S. Cl. ..................................................... 556/442
[58] Field of Search ........................................ 556/442

[56] References Cited

U.S. PATENT DOCUMENTS

| | | | |
|---|---|---|---|
| 4,085,137 | 4/1978 | Mitsch et al. | 556/442 X |
| 4,308,212 | 12/1981 | Takanizawa et al. | 556/442 X |
| 4,689,181 | 8/1987 | Blatch | 556/442 X |
| 4,748,225 | 5/1988 | Yoshioka et al. | 556/442 X |

Primary Examiner—Paul F. Shaver

Attorney, Agent, or Firm—Oblon, Spivak, McClelland, Maier & Neustadt

[57] ABSTRACT

A fluorine-containing organosilicon compound according to the present invention is expressed by the general formula:

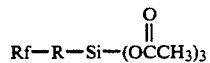

wherein Rf is a perfluoropolyether group having 3 to 17 carbon atoms, R is an alkylene group having 1 to 6 carbon atoms or an ether group expressed by the general formula:

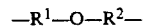

wherein $R^1$ and $R^2$ may be the same or different and are each alkylene groups having 1 to 6 carbon atoms. The fluorine-containing organosilicon compound is highly useful as a curing agent for organopolysiloxane compositions that are condensation curable at room temperature.

4 Claims, 2 Drawing Sheets

FLUORINE-CONTAINING ORGANOSILICON COMPOUND

BACKGROUND OF THE INVENTION

1. Field of the Invention

The present invention relates to a novel organosilicon compound useful as a curing agent for organopolysiloxane compositions that are condensation curable at room temperature.

2. Description of the Prior Art

Various organosilicon compounds having hydrolyzable groups are known in the art as a curing agent for organopolysiloxane compositions that are condensation curable at room temperature.

Such prior art curing agent, however, is defective in that it contaminates the surface of the cured product and its environment and that said organopolysiloxane compositions when used as a sealing, coating or electric insulation material will impair the appearance and electrical characteristics of a device.

SUMMARY OF THE INVENTION

The present invention therefore aims at providing a novel organosilicon compound which is useful as a curing agent for organopolysiloxane compositions that are condensation curable at room temperature and which can effectively avoid aforementioned contamination of the cured product at the surface.

According to the present invention, there is provided a fluorine-containing organosilicon compound having the following general formula (1):

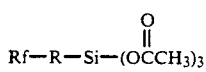

wherein Rf is a perfluoropolyether group having 3 to 17 carbon atoms, and R is an alkylene group having 1 to 6 carbon atoms, or an ether group expressed by the general formula: $-R^1-O-R^2-$ wherein $R^1$ and $R^2$ may be the same or different and are each alkylene groups having 1 to 6 carbon atoms.

DETAILED DESCRIPTION OF THE INVENTION

Fluorine-containing Orcanosilicon Compound

Figure 1:
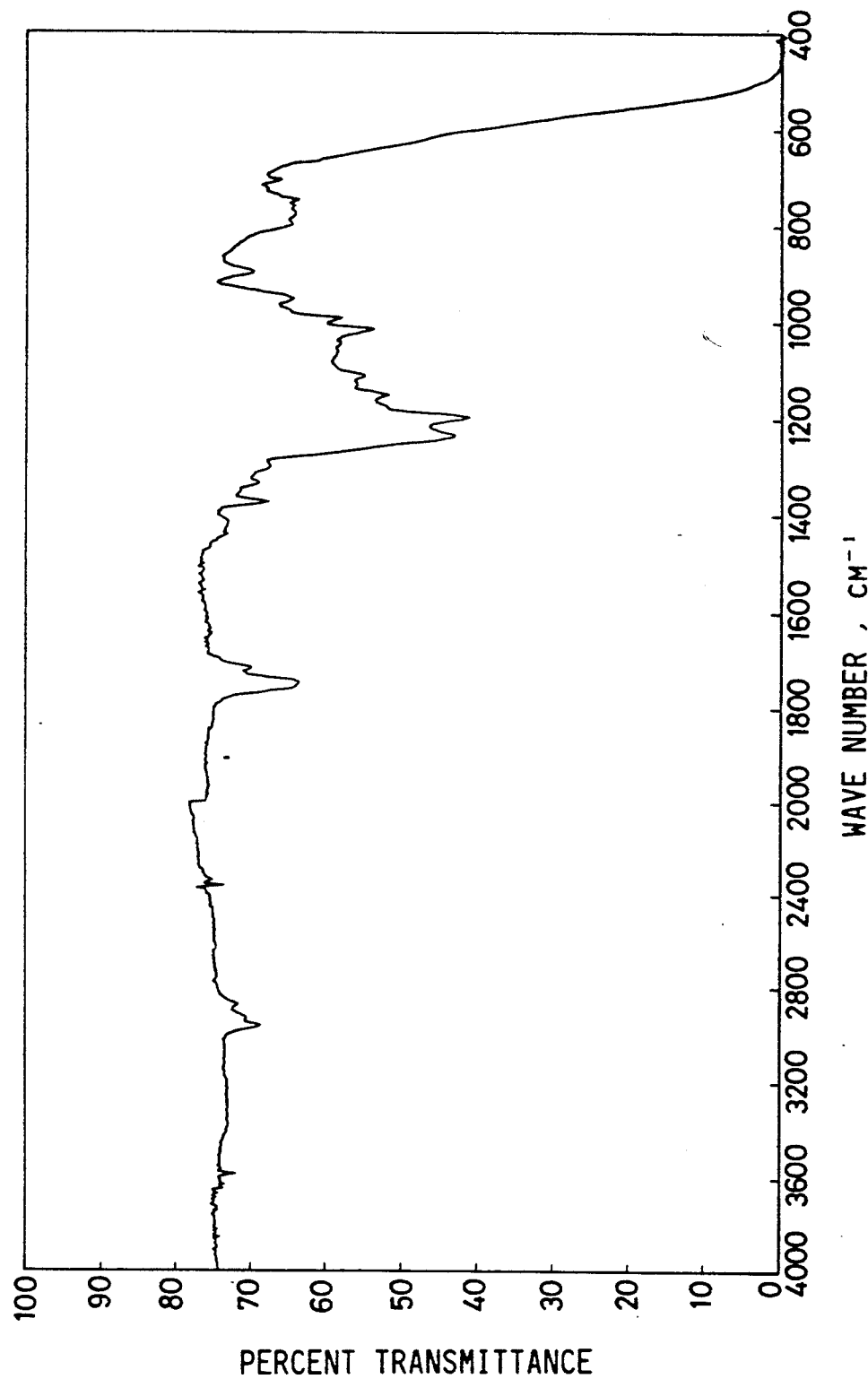
FIG. 1 shows IR spectrum of a fluorine-containing organosilicon compound of the present invention obtained in Example 1.

In the general formula (1) representing the fluorine-containing organosilicon compound according to the present invention, Rf represents a perfluoropolyether group having 3 to 17 carbon atoms which may be linear or branched. Typical examples of the perfluoropolyether group include:

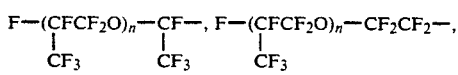

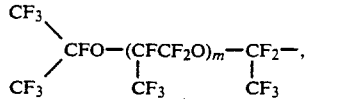

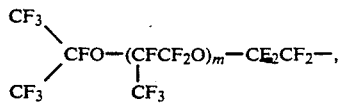

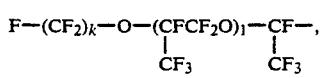

and

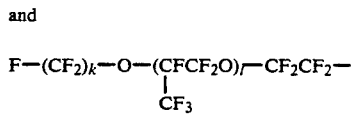

wherein n is an integer of from 1 to 5, m an integer of 0 or from 1 to 4, k an integer of from 1 to 12 and l an integer of from 1 to 7.

In the general formula (1), R represents an alkylene group of 1 to 6 carbon atoms such as methylene group, ethylene group, propylene group, butylene group, pentylene group or hexylene group. Alternatively, it represents a divalent ether group which comprises two or more of said alkylene groups bonded with each other via an oxygen atom. In other words, the ether group is expressed by the formula $-R^1-O-R^2-$ wherein $R^1$ and $R^2$ each denote an alkylene group of 1 to 6 carbon atoms.

Specific examples of fluorine-containing organosilicon compound represented by the general formula (1) include but are not limited to the following.

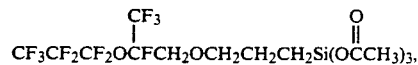

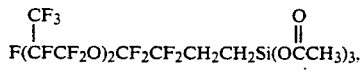

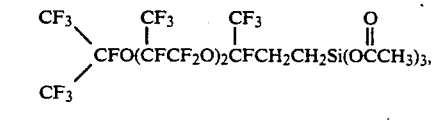

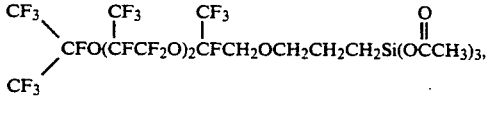

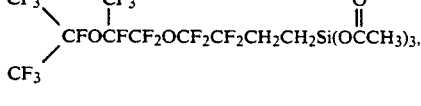

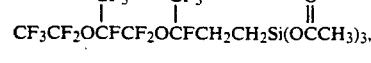

-continued

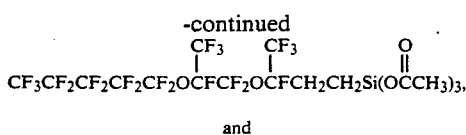

and

Method of Production

The fluorine-containing organosilicon compound of the present invention of the general formula (1) can be synthesized from fluorine-containing trichlorosilane of the general formula (2):

$$Rf\text{---}R\text{---}SiCl_3 \quad (2)$$

wherein Rf and R are as defined above, by (A) adding thereto acetic anhydride to cause a reaction for elimination of acetyl chloride, or by (B) adding thereto alkali metal salt of acetic acid such as potassium acetate and sodium acetate to cause the elimination of a salt.

As for the method (A), the amount of acetic anhydride to be used is preferably between 3.0 and 4.0 mol per mol of the fluorine-containing trichlorosilane, and more preferably between 3.3 and 4.5 mol. The reaction temperature can be suitably adjusted depending on the reactivities of the fluorine-containing trichlorosilane and acetic anhydride and on other conditions. Preferable reaction temperature is in the range of from 20° to 150° C., and more preferably between 50° and 100° C. The reaction time is normally between one and 50 hours, and more particularly between 5 and 20 hours.

As for the method (B), the amount of the alkali metal salt of acetic acid is preferably between 3.0 and 6.0 mol per mol of the fluorine-containing trichlorosilane, and more preferably between 3.3 and 4.5 mol. The reaction temperature can be suitably adjusted depending on the reactivities of the fluorine-containing trichlorosilane and the alkali metal salt of acetic acid and on other conditions. Preferable reaction temperature is between 50° and 200° C., and more preferably between 80° and 150° C. The reaction time is generally between one to 50 hours, and more particularly between 5 to 20 hours. According to the method (B), the alkali metal salt of acetic acid may be dissolved in a solvent prior to use. Such solvents include, for example, hydrocarbons such as benzene, toluene, xylene and hexane.

Use

The novel fluorine-containing organosilicon compound according to the present invention is applicable to various uses. The compound is particularly useful as a curing agent for organopolysiloxane compositions that contain as a major ingredient an organopolysiloxane terminated with silicon-bonded OH radicals, alkoxy radicals or the like and are condensation curable at room temperature. Products obtained by curing the compositions have excellent properties such as resistance to contamination, water and oil repellencies, and chemical resistance due to the introduced perfluoropolyether group. These compositions may be used as high performance sealing, coating and electric insulation materials.

EXAMPLE 1

Into a 500 ml four-necked flask attached with an ether adaptor, 137.1 g (1.34 mol) of acetic anhydride was charged and heated to 50° C. Into the flask was added dropwise with a dropping funnel over one hour 200 g (0.33 mol) of a fluorine-containing trichlorosilane of the general formula:

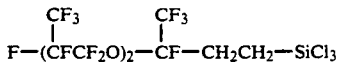

Upon completion of the addition, the system was heated at 60° to 100° C. for 10 hours under stirring with the by-produced acetyl chloride being removed from the ester adaptor. The resultant reaction mixture was then distilled to obtain 169.2 g of fraction having a boiling point of 135° C./4mmHg.

To confirm the molecular structure of the fraction thus obtained, element analysis, IR spectrophotometry and $^1$H-NMR spectrophotometry were conducted, and the following results were obtained. Element analysis:

| | Element analysis | | | |
|---|---|---|---|---|
| | C(%) | H(%) | Si(%) | F(%) |
| | (in terms of $C_{16}H_{13}O_8F_{17}Si_1$) | | | |
| Calculated | 28.1 | 1.9 | 4.1 | 47.2 |
| Found | 28.0 | 1.9 | 4.0 | 47.4 |

IR spectrum: As shown in FIG. 1.
C=O: 1750 cm$^{-1}$
$^1$H - NMR spectrum; internal standard: CHCl$_3$ in CCl$_4$
δ (ppm)
0.8–1.4 (m, 2H, S—CH$_2$—C)
2.0 (s, 9H, —COCH$_3$)
2.1–2.7 (m, 2H, Si—C—CH$_2$—C)

These results confirmed that the fraction obtained is an organosilicon compound of the formula (yield 76%):

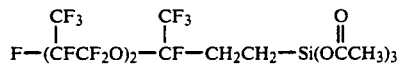

EXAMPLE 2

Example 1 was repeated, except that in place of the fluorine-containing trichlorosilane used in Example 1, 200 g (0.41 mol) of a fluorine-containing trichlorosilane represented by the following formula:

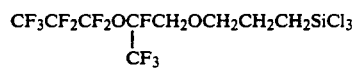

was used and the amount of acetic anhydride was changed to 164.5 g (1.61 mol), thereby obtaining 188.9 g of a fraction having a boiling point of 129° C./2 mmHg.

To confirm the molecular structure of the fraction thus obtined, elemental analysis, IR spectrophotometry and $^1$H-NMR spectorphotometry were conducted, and the following results were obtined.

| | Elemental analysis | | | |
|---|---|---|---|---|
| | C(%) | H(%) | Si(%) | F(%) |
| | (in terms of $C_{15}H_{17}O_8F_{11}Si_1$) | | | |
| Calculated | 32.0 | 3.0 | 5.0 | 37.2 |
| Found | 31.8 | 2.9 | 5.2 | 37.3 |

Figure 2:
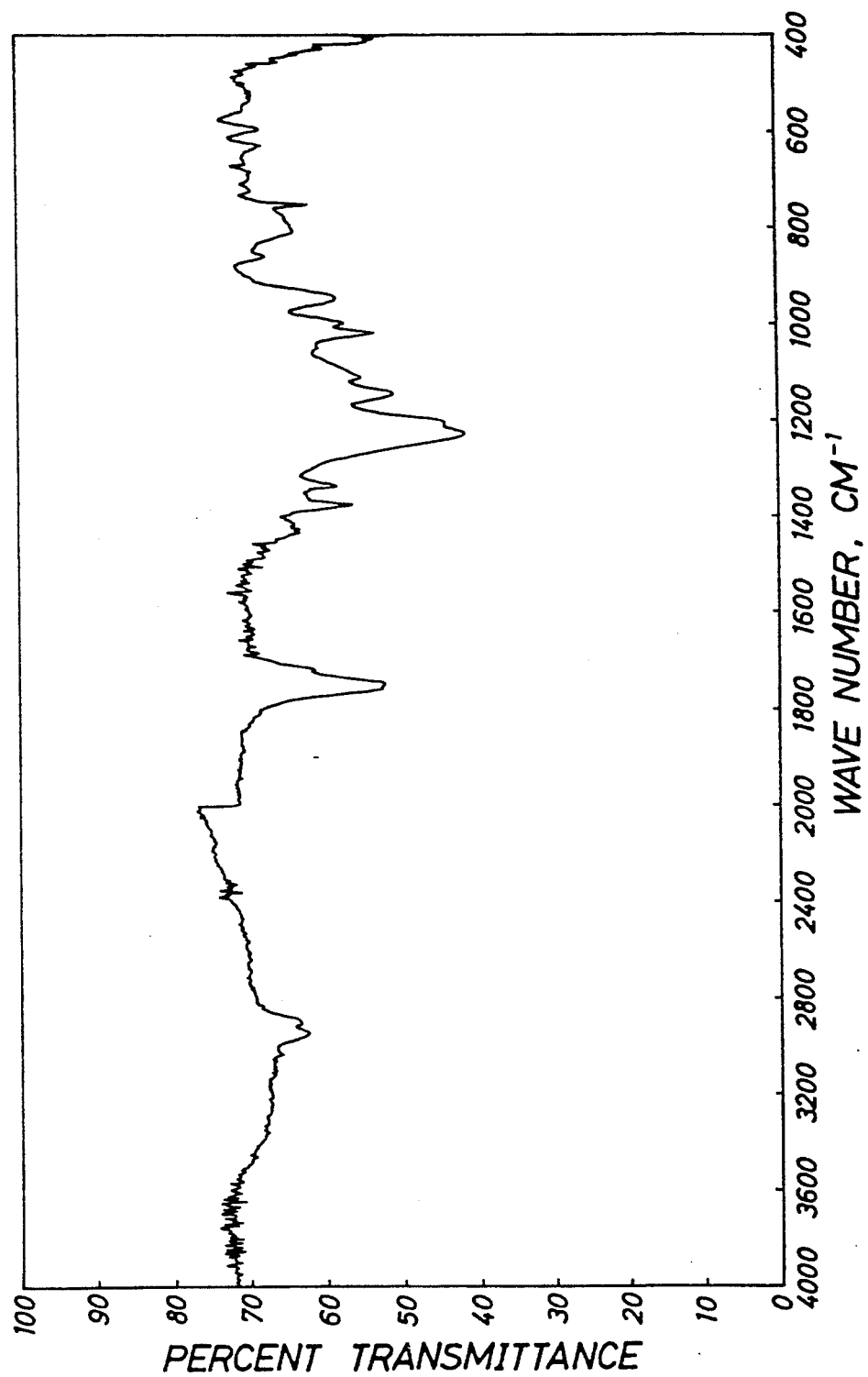
FIG. 2 shows an infrared absorption spectrum of the fluorine-containing organosilicon compound according to the present invention obtained in Example 2.

IR spectrum: As shown in FIG. 2.
C=O: 1750 cm$^{-1}$
$^1$H-NMR spectrum; internal standard: CHCl$_3$ in CCl$_4$ δ (ppm)
0.9-1.4 (m, 2H, Si—CH$_2$—C)
1.5-2.0 (m, 2H, Si—C—CH$_2$—C)
2.1 (s, 9H, —COCH$_3$)
3.4-3.6 (t, 2H, Si—C—C—CH$_2$—C)
3.8-4.1 (d, 2H, Si—C—C—C—O—CH$_2$—C)

Based on the results, it has been confirmed that the fraction obtained is an organosilicon compound of the formula:

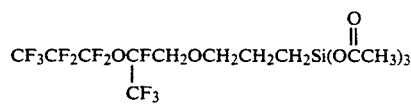

Yield: 82%

What we claim is:

1. A fluorine-containing organosilicon compound of the general formula (1):

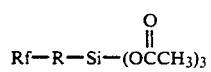 (1)

wherein Rf is a perfluoropolyether group having 3 to 17 carbon atoms, and R is an alkylene group having 1 to 6 carbon atoms or an ether group of the formula: —R$^1$—O—R$^2$— wherein R$^1$ and R$^2$ may be the same or different and are each alkylene groups having 1 to 6 carbon atoms.

2. The fluorine-containing organosilicon compound as claimed in claim 1, wherein Rf in said general formula (1) is represented by

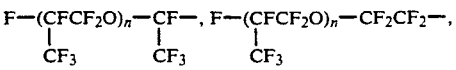

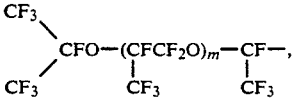

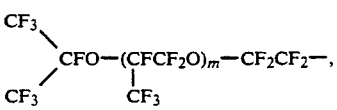

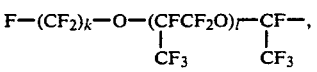

or

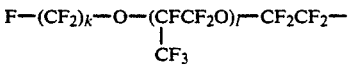

wherein n is an integer of 1 to 5, m an integer of 0 or 1 to 4, k an integer of 1 to 12 and l an integer of 1 to 7.

3. The fluorine-containing organosilicon compound as claimed in claim 1, wherein Rf in said general formula (1) is

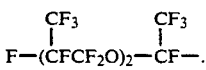

4. The fluorine-containing organosilicon compound as claimed in claim 1, wherein R in said general formula (1) is —CH$_2$CH$_2$— or —CH$_2$O—CH$_2$CH$_2$CH$_2$—.

* * * * *